Figure 1:
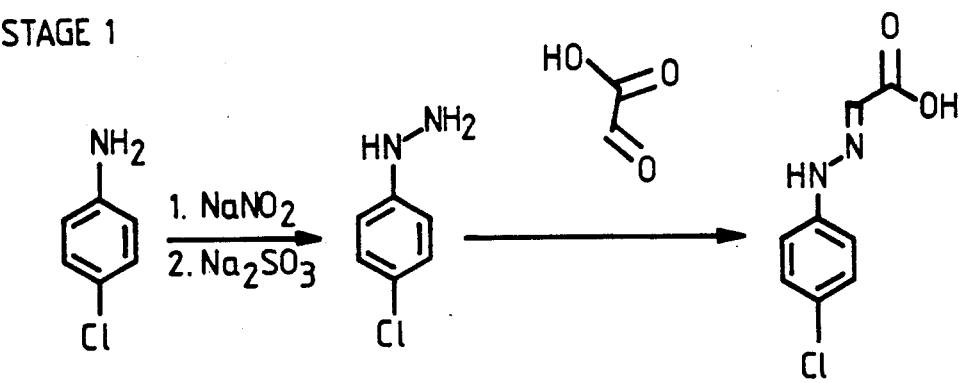
Figure 1:
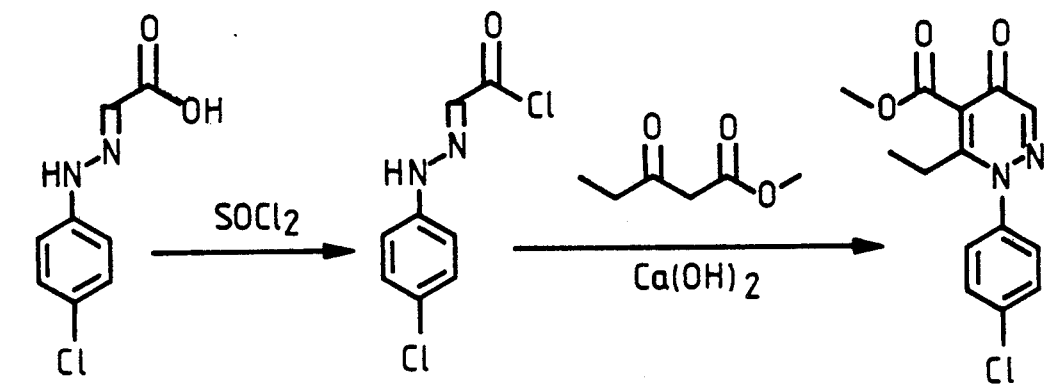
Figure 1:
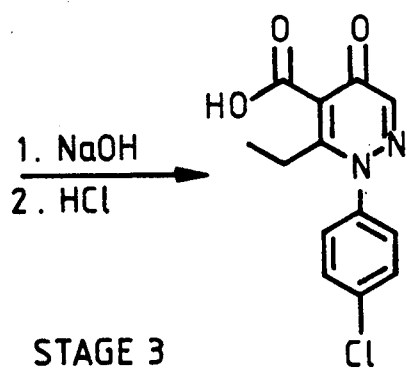
Figure 1:
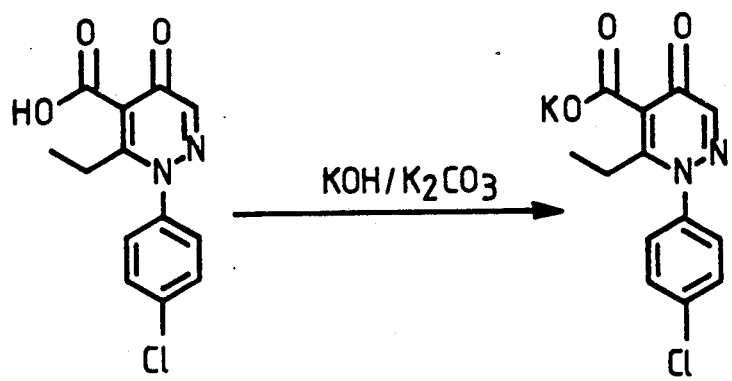

United States Patent [19]

Cox et al.

[11] Patent Number: 5,189,163

[45] Date of Patent: Feb. 23, 1993

[54] METHOD OF PREPARING PYRIDAZINONE DERIVATIVES

[75] Inventors: Brian G. Cox, Cheshire; Michael S. Howarth, Lancashire, both of England

[73] Assignee: Imperial Chemical Industries PLC, London, England

[21] Appl. No.: 858,161

[22] Filed: Mar. 13, 1992

Related U.S. Application Data

[63] Continuation of Ser. No. 574,675, Aug. 30, 1990, abandoned.

[30] Foreign Application Priority Data

Aug. 30, 1989 [GB] United Kingdom ............... 8919622

[51] Int. Cl.$^5$ ............................................. C07D 237/24
[52] U.S. Cl. ................................................ 544/239
[58] Field of Search .................................... 544/239

[56] References Cited

U.S. PATENT DOCUMENTS

| | | | |
|---|---|---|---|
| 2,839,532 | 6/1958 | Druey et al. | 544/239 |
| 4,238,490 | 12/1980 | Powers et al. | 544/239 |
| 4,281,125 | 7/1981 | Depompei et al. | 544/239 |
| 4,661,145 | 4/1987 | Fujimoto et al. | 544/239 |
| 4,732,603 | 3/1988 | Patterson | 544/239 |
| 5,003,068 | 3/1991 | McLaughlin | 544/239 |

FOREIGN PATENT DOCUMENTS

| | | | |
|---|---|---|---|
| 0049971 | 4/1982 | European Pat. Off. | |
| 0136974 | 4/1985 | European Pat. Off. | |
| 0359435 | 3/1990 | European Pat. Off. | 544/239 |
| 0359438 | 3/1990 | European Pat. Off. | 544/239 |
| 0359474 | 3/1990 | European Pat. Off. | |
| 858792 | 1/1961 | United Kingdom | |

OTHER PUBLICATIONS

Chem. Abstr. vol. 113 entry 115326e abstracting EP359474 (1990).
Chem. Abstr. vol. 113 entry 152447r abstracting EP 359438 (1990).
House, H. O., Modern Synthetic Reactions, (W. A. Benjamin, Inc., 1972) pp. 763 and 766.
von Dieter Seebach et al., Herstellung von 1,3 von 1,3-Diketonen under von Nitro-diketonen durch (1:1)-Acylierungen von Lithiumenolaten mit Acylchloriden, Helvetica Chimica Acta, vol. 64, (1981), pp. 716 and 718.
House, H. O. et al., The Chemistry of Carbanions, XXII, c-vs, O-Acylation of Metal Enola, J. Org. Chem., vol. 38 No. 3, 1973, pp. 514–515.

*Primary Examiner*—Donald G. Daus
*Attorney, Agent, or Firm*—Cushman, Darby & Cushman

[57] ABSTRACT

A method for the preparation of a pyridazinone derivative having the general formula I:

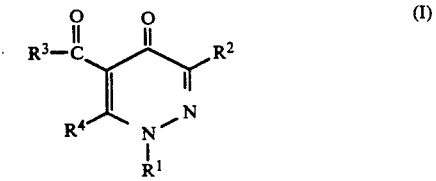

where: $R^1$ is a phenyl group, optionally substituted, $R^2$ is H, alkyl or carboxy, $R^3$ is H, alkyl or alkoxy and $R^4$ is alkyl; said method comprising reacting a hydrazone of glyoxylic acid halide having the formula VII:

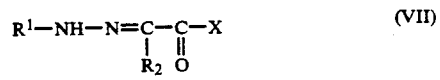

in which X is halogen, with an ester of formula VIII;

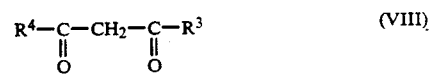

in the presence of an alkaline earth base.

8 Claims, 1 Drawing Sheet

STAGE 1

STAGE 2

STAGE 3

METHOD OF PREPARING PYRIDAZINONE DERIVATIVES

This is a continuation of application Ser. No. 07/574,675, filed on Aug. 30, 1990, which was abandoned upon the filing hereof.

This invention relates to a method for the preparation of derivatives of pyridazinone which are useful as plant growth regulating compounds, and in particular as chemical hybridising agents. They have found use as male sterilants for cereal crops, for example wheat and barley, and are useful for making hybrids in such crops.

British Patent No. 858,792 describes the preparation of derivatives of pyridazinone which have the formula I:

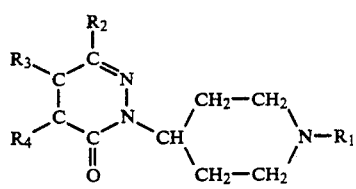

in which $R_1$ is an alkyl group having from 1 to 4 carbon atoms, either $R_2$ is an alkyl group containing 1 to 4 carbon atoms or a phenyl or thiophene residue which may be substituted, $R_3$ is hydrogen or an alkyl group having from 1 to 4 carbon atoms, or $R_2$ and $R_3$ together represent an alkylene chain, and $R_4$ is hydrogen or an alkyl, aryl or cyano group. Two procedures are described therein: the first comprises condensation of an appropriate N-alkyl-piperidyl-4-hydrazine with a γ-keto-carboxylic acid, followed by dehydrogenation of the condensation product. The second procedure involves condensing a N-alkyl-piperidyl-4-hydrazine with an α-dicarbonyl derivative to form a mono- hydrazone which is then reacted with a carboxylic acid having a reactive methylene group, or its alkyl ester.

It is known from European Patent Application No. 49971 to manufacture pyridazinone compounds according to the following reaction scheme.

Stage 1: Diazo-coupling

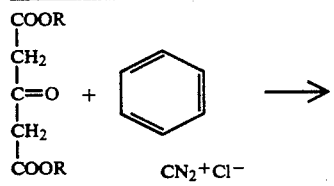

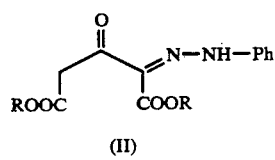

Stage 2: Ring Closure $$II + NaOH, R^1COCl \longrightarrow$$

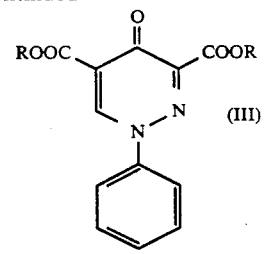

The compound (III) so obtained may then be hydrolysed either partially to the mono ester or completely to the dicarboxylic acid; and if desired, the resulting dicarboxylic acid may be partially decarboxylated. This generally gives a mixture of the two possible monocarboxylic acids, from which the desired product may be recovered. A problem with the above process is a tendency for polychlorinated biphenyls (PCBs) to be produced in Stage 1 (diazo-coupling). This is most undesirable, as PCBs are toxic and persist in the environment: accordingly considerable care and expense must be undertaken to recover them from the reaction mixture and dispose of them safely. In addition, the overall yield of the 3-carboxy derivative is 34% and no description is given in the European Application as to how the hydrolysis and decarboxylation stages necessary to obtain the 3-unsubstituted derivative has been given in the said European Application. However, one may estimate, using figures given for similar steps in am alternative procedure, that an overall yield of final product will be around 21% at best.

There has been previously proposed (British Patent Application No. 8821447.3) a method for the manufacture of 4-pyridazinone carboxylic acids of formula:

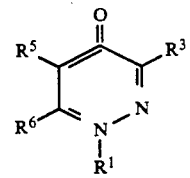

where: $R^1$ is a phenyl group, optionally substituted with, e.g. alkyl or halo groups, $R^3$ is H, alkyl, halo or carboxy groups, at least one of $R^3$ and $R^5$ being carboxy; $R^5$ is a carboxy group. Our method uses a novel cyclisation step which avoids Stage 1 of the scheme set out above, in which PCBs are produced in undesirable quantities, the method comprising reacting a phenylhydrazone of a glyoxylic acid halide with an enamine derivative of a ketoester. The principal disadvantages of the proposed procedure are modest yield and the tendency to formation of glyoxylic acid amides as by-products. The method may be readily understood from the following reaction scheme:

Step 1

-continued

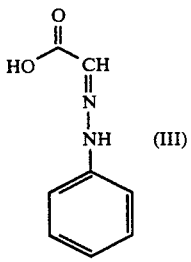

Step 2

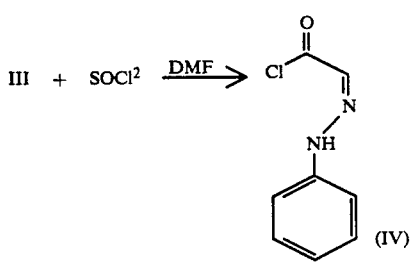

Step 3

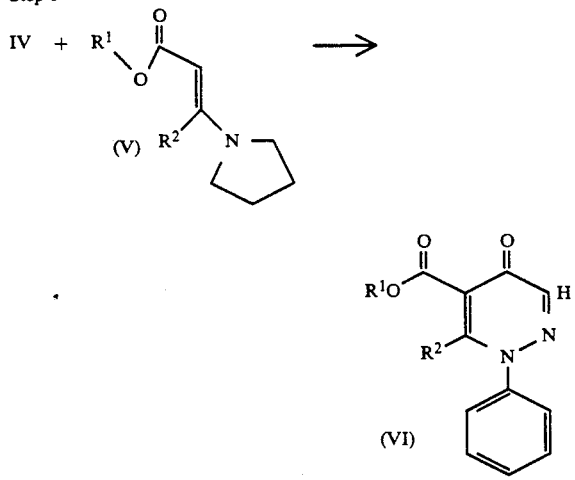

The ester (VI) so obtained may be readily hydrolysed with strong alkali to the corresponding sodium or potassium salt, a convenient form for use as a plant growth regulant or chemical hybridising agent.

An object of the present invention is to obviate or mitigate the aforesaid disadvantages.

According to the present invention there is provided a method for the preparation of a pyridazinone derivative having the general formula I:

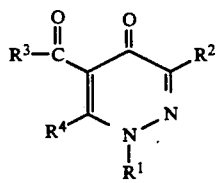

where: $R^1$ is a phenyl group, optionally substituted with, e.g. alkyl or halo groups, $R^2$ is H, alkyl, or carboxy groups, $R^3$ is hydroxy or an alkyl or alkoxy group and $R^4$ is an alkyl group; said method comprising reacting a hydrazone of glyoxylic acid halide having the formula VII:

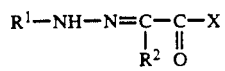

in which X represents a halogen atom and $R^1$ and $R^2$ are as defined above, with an oxo-carboxylic acid ester having the formula VIII;

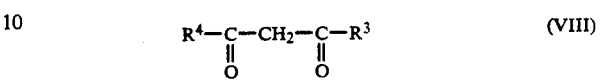

in which $R^3$ is an alkyl or alkoxy group and $R^4$ is as defined above, in the presence of an alkaline earth base. Optionally, where $R^3$ is alkoxy, the product may then be hydrolysed to $R^3 = -OH$.

In a modification of the method of the invention a compound of formula I may be prepared by reaction of a compound of formula VII with a preformed complex of the compound of formula VIII with the alkaline earth base.

For the purposes of this invention the term "alkaline earth base" means the oxides and hydroxides of the true alkaline earths calcium, strontium and barium, as well as of the similar element lithium.

The invention also includes the preparation of salts of the compound of general formula I above by treatment with an alkali metal compound.

In a preferred embodiment of the invention the groups $R^1$ to $R^4$ in formula I have the following meanings:

$R^1$ is 4-chlorophenyl; $R^2$ is hydrogen; $R^3$ is hydroxy or alkoxy, preferably methoxy or ethoxy; and $R^4$ is ethyl.

The reaction may be conducted in a two-phase aqueous/organic system. However, it is preferred that the reaction be conducted in the presence of alkaline earth metal (particularly calcium) hydroxide in an organic liquid medium.

FIG. I of the drawings shows a reaction scheme leading from p-chloroaniline to a final product compound 1-(4-chlorophenyl)-1,4-dihydro-6-ethyl-4-oxopyridazine-5-carboxylic acid. The invention will now be described, by way of illustration, in the following Examples.

EXAMPLE 1

(a) Preparation of the 4-chlorophenyl hydrazone of glyoxylic acid chloride 4-chlorophenyl hydrazone of glyoxylic acid (56.4 g at 88% purity=0.25 mole) was suspended in a mixture of hexane (500 ml) and dimethylformamide (DMF) (3.1 g). Thionyl chloride (32.8g=0.275 mole) was added over a period of 15 minutes at ambient temperature and the mixture stirred, also at ambient temperature until gas evolution ceased. The crude product was filtered off, washed with hexane, and dried by drawing air through the product on the filter paper. The product was transferred to a beaker, methanol (100 ml) was added and the mixture stirred for about 30 seconds. The product was filtered, washed with a small amount of methanol, and dried under suction. The product was then completely dried in a desiccator.

The weight of product recovered was 52.4 g with a melting point of 123°-124° C. The strength by NMR was 93.7% and the yield was 93.7%.

(b) Preparation of 1-(4-chlorophenyl)-1,4-dihydro-6-ethyl-4-oxopyridazine-5-carboxylic acid 4-chlorophenyl hydrazone of glyoxylic acid chloride (10 g at 97% = 0.045 mole) methyl-3-oxopentanoate (6 g at 97% = 0.045 mole) and toluene (100 ml) were charged to a reaction vessel and stirred together for 5 minutes at ambient temperature. Calcium hydroxide (3.5 g at 96% = 0.045 mole) was then added. The temperature rose to about 40° C. The reactants were stirred for a further 15 minutes and then 1M hydrochloric acid (100 ml) was added. The mixture was stirred for a further 5 minutes then the two phases were separated. The toluene phase was recharged to the vessel an 1M sodium hydroxide was added. The mixture was heated at 60°–65° C. for two hours then cooled and the two phases separated. The sodium hydroxide solution was added to a rapidly stirred mixture of concentrated hydrochloric acid (20 ml) and water (30 ml) at ambient temperature over about 15 minutes. The product was recovered by filtration, washed until chloride free with water and dried at 30°–35° C. and 30 mm Hg pressure. The weight of product recovered was 11.3 g, representing a 70.2% yield. The strength by NMR was 76.5%.

EXAMPLES 2–9

Further compounds of general formula IX shown below were made by the method of the invention. Structures and data for such compounds are summarised in the Table below.

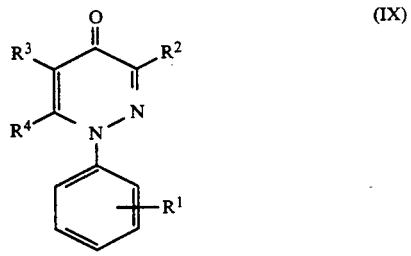

(IX)

EXAMPLE 2

Preparation of 1-(4-chlorophenyl)-1,4-dihydro-6-methyl-4-oxo-pyridazine-5-carboxylic acid Calcium hydroxide (4.7 g at 98% = 0.062 mole) was added to a beaker containing a stirred solution of ethylacetoacetate (96.6 g at 98% = 0.05 mole) and toluene (50 ml) and stirred for 2 hours at ambient temperature. The contents were then added to a reaction vessel containing 4-chlorophenyl hydrazone of glyoxylic acid chloride (11.3 g at 96% = 0.05 mole) and toluene (100 mls) and stirred for 2 hours at ambient temperature. A 2M hydrochloric acid solution (100 mls) was added and stirred for 5 minutes; then the two phases were separated. The toluene phase was recharged to the vessel and heated for 2 hours at 80° C. The contents were cooled to 50° C. and 10% sodium hydroxide solution (50 g) was added. The mixture was then heated at 60°–65° C. for 3 hours then cooled and the two phases separated. The sodium hydroxide phase was added to a rapidly stirred mixture of concentrated sulphuric acid (5.9 g) and water (54.1 g) at ambient temperature over 1 hour. The crude product was recovered by filtration, washed with water until sulphate free and pulled fairly dry. The crude product was charged to isopropanol (25 mls) and heated at reflux for 1 hour before cooling to 20° C. The purified material was recovered by filtration and washed with cold isopropanol, then dried at 40°–50° C. and 20 mm Hg pressure.

EXAMPLE 3

Preparation of 1-(4 chlorophenyl)-1,4-dihydro-4-oxo-6-n-propyl-pyridazine-5-carboxylic acid Calcium hydroxide (4.7 g at 98% = 0.062 mole) was added to a beaker containing a stirred solution of ethyl butyrylacetate (8.1 g at 98% = 0.05 mole) and toluene (50 ml) and stirred for 2 hours at ambient temperature. The contents were then added to a reaction vessel containing 4-chlorophenyl hydrazone of glyoxylic acid chloride (11.3 g at 96% = 0.05 mole) and toluene (100 mls) and stirred for 2 hours at ambient temperature. A 2M hydrochloric acid solution (100 mls) was added and stirred for 5 minutes; then the two phases were separated. The toluene phase was recharged to the vessel and heated for 2 hours at 80° C. The contents were cooled at 50° C. and 10% sodium hydroxide solution (50 g) was added. The mixture was then heated at 60°–70° C. for 3 hours then cooled and the two phases separated.

The sodium hydroxide phase was added to a rapidly stirred mixture of concentrated sulphuric acid (5.9 g) and water (54.1 g) at ambient temperature over 1 hour. The crude product was recovered by filtration, washed

| Example | $R^1$ | $R^2$ | $R^3$ | $R^4$ | M.P., °C. lit/found | Microanalysis C | H | N % |
| --- | --- | --- | --- | --- | --- | --- | --- | --- |
| 2 | 4-Chloro | H | COOH | $CH_3$ | 207.8/ 208.10 | 54.4 54.0 | 3.4 3.3 | 10.6 10.9 |
| 3 | 4-Chloro | H | COOH | $nC_3H_2$ | 171–2/ 175–77 | 57.4 57.2 | 4.4 4.6 | 9.6 9.3 |
| 4 | 4-Chloro | H | $COC_2H_5$ | $C_2H_5$ | New/ 89–90 | 62.0 01.4 | 5.2 5.3 | 9.6 9.3 |
| 5 | 4-Chloro | $CH_3$ | COOH | $C_2H_5$ | New/ 210–12 | 57.4 57.4 | 4.4 4.5 | 9.6 9.5 |
| 6 | 2-$CH_3$ | H | COOH | $C_2H_5$ | New/ 175–6 | 65.1 65.5 | 5.4 5.7 | 10.9 10.2 |
| 7 | 3-Chloro | H | COOH | $C_2H_5$ | New/ 175–7 | 56.0 55.3 | 3.9 3.6 | 10.1 10.0 |
| 8 | 4-$CH_3$ | H | COOH | $C_2H_5$ | New/ 186–7 | 65.1 65.5 | 5.4 5.8 | 10.9 10.9 |
| 9 | 4-Bromo | H | COOH | $C_2H_5$ | 220, dec./ 196–8, dec | 48.3 49.2 | 3.4 3.4 | 8.7 8.1 | with water until sulphate free and pulled fairly dry. The crude product was charged to isopropanol (25 mls) and heated at reflux for 1 hour before cooling to 20° C. The purified material was recovered by filtration and washed with cold isopropanol then dried at 40°-50° C. and 20 mm Hg pressure.

EXAMPLE 4

Preparation of 1-(4-chlorophenyl)-1,4-dihydro-6-ethyl-4-oxo-5-propionyl-pyridazine Calcium hydroxide (4.7 g at 98%=0.062 mole) was added to a heater containing a stirred solution or hepta-3,5-dione (6.5 g at 98%=0.05 mole) and toluene (50 ml) and stirred for 2 hours at ambient temperature. The contents were then added to a reaction vessel containing 4-chlorophenyl hydrazone of glyoxylic acid chloride (11.3 g at 96%=0.05 mole) and toluene (100 mls) and stirred for 2 hours at ambient temperature. A 2M hydrochloric acid solution was added and stirred for 5 minutes then the two phases were separated. The toluene phase was recharged to the vessel and heated for 30 minutes at 80° C. and then cooled to 25° C. The toluene was removed using a rotary evaporator leaving a dark brown oil. The crude solid product was crystallised from diisopyropyl ether and subsequently recrystallised using the same solvent.

EXAMPLE 5

Preparation of 1-(4-chlorophenyl)-1,4-dihydro-6-ethyl-3-methyl-4-oxo-pyridazine-5-carboxylic acid 4-Chlorophenyl hydrazone of pyruvic acid (11.0 g at 97%=0.05 mole), dimethyl formamide (0.6 g) and n-hexane (100 ml) were charged to a reaction vessel and thionyl chloride (6.5 g=0.055 mole) was added over 5 minutes with stirring at ambient temperature. The contents were stirred for 2 hours at ambient temperature before decanting off the hexane and replacing it with toluene (100 ml). A calcium hydroxide/ methyl-3-oxopentanoate complex, made by stirring together methyl-3-oxopentanoate (6.6 g at 98%=0.05 mole), calcium hydroxide (4.7 g at 98%=0.062 mole) and toluene (50 ml) for 2 hours at ambient temperature was added to the reaction vessel and the contents were stirred for 2 hours at ambient temperature. A 2M hydrochloric acid solution (100 mls) was added and stirred for 5 minutes; then the two phases were separated. The toluene phase was recharged to the vessel and heated at 80° C. for 2 hours. The contents were cooled to 50° C. and 10% sodium hydroxide solution (50 g) was added. The mixture was then heated at 60°-70° C. for 3 hours, cooled, and the two phases separated. The sodium hydroxide phase was added to a rapidly stirred mixture of concentrated sulphuric acid (5.9 g) and water (54.1 g) at ambient temperature over 1 hour. The crude product was recovered by filtration, washed with water until sulphate free and pulled fairly dry.

the crude product was charged to isopropanol (25 mls) and heated at reflux for 1 hour before cooling to 20° C. The purified product was recovered by filtration and washed with cold isopropanol then dried at 40°-50° C. and 20 mm Hg pressure.

EXAMPLE 6

Preparation of 1-(2-methylphenyl)-1,4-dihydro-6-ethyl-4-oxo-pyridazine-5-carboxylic acid 2-Methylphenyl hydrazone of glyoxylic acid (9.2 g at 97%=0.05 mole), dimethyl formamide (0.06 g) and n-hexane (100 ml) were charged to a reaction vessel and thionyl chloride (6.5 g=0.055 mole) was added over 5 minutes with stirring at ambient temperature. The contents were stirred for 2 hours at ambient temperature before decanting off the hexane and replacing it with toluene (100 ml). A calcium hydroxide/methyl-3-oxopentanoate complex, made by stirring together methyl-3-oxopentanoate (6.6 g at 98%=0.05 mole), calcium hydroxide (4.7 g at 98%=0.062 mole) and toluene (50 ml) for 2 hours at ambient temperature, was added to the reaction vessel and the contents were stirred for 2 hours at ambient temperature. A 2M hydrochloric acid solution (100 mls) was added and stirred for 5 minutes then the two phases were separated. The toluene phase was recharged to the vessel and heated at 80° C. for 2 hours. The contents were cooled at 50° C. and 10% sodium hydroxide solution (50 g) was added. The mixture was then heated at 60°-70° C. for 3 hours then cooled and the two phases separated. The sodium hydroxide phase was added to a rapidly stirred mixture of concentrated sulphuric acid (5.8 g) and water (54.1 g) at ambient temperature over 1 hour.

The crude product was recovered by filtration, washed with water until sulphate free and pulled fairly dry. The crude product was charged to isopropanol (25 ml) and heated at reflux for 1 hour before cooling to 20° C. The purified product was recovered by filtration and washed with cold isopropanol then dried at 40°-50° C. and 20 mm Hg pressure.

EXAMPLE 7

Preparation of 1-(3-chlorophenyl)-1,4-dihydro-6-ethyl-4-oxo-pyridazine-5-carboxylic acid 3-Chlorophenyl hydrazone of glyoxalic acid (10.2 g at 97%=0.05 mole), dimethyl formamide (0.06 g) and n-hexane (100 ml) were charged to a reaction vessel and thionyl chloride (6.5 g=0.055 mole) was added over 5 minutes with stirring at ambient temperature. The contents were stirred for 2 hours at ambient temperature before decanting off the hexane and replacing it with toluene (100 mls). The calcium hydroxide/methyl-3-oxopentanoate complex made by stirring together methyl-3-oxopentanoate (6.6 g at 98%=0.05 mole), calcium hydroxide (4.7 g at 98%=0.062 mole) and toluene (50 ml) for 2 hours at ambient temperature was added to the reaction vessel and the contents were stirred at ambient temperature for 2 hours. A 2M hydrochloric acid solution (100 mls) was added and stirred for 5 minutes; then the two phases were separated. The toluene phase was recharged to the vessel and heated for 2 hours at 80° C. The contents were cooled to 50° C. and 10% sodium hydroxide solution (50 g) was added. The mixture was then heated at 60°-70° C. for 3 hours, then cooled and the two phases separated. The sodium hydroxide phase was added to a rapidly stirred mixture of concentrated sulphuric acid (5.9 g) and water (54.1 g) at ambient temperature over 1 hour.

The crude product was recovered by filtration, washed with water until sulphate free and pulled fairly dry. It was then charged to isopropanol (25 ml) and heated at reflux for 1 hour before cooling to 20° C. The purified material was recovered by filtration and washed with cold isopropanol then dried at 40°-50° C. and 20 mm Hg pressure.

EXAMPLE 8

Preparation of 1-(4-methylphenyl)-1,4-dihydro-6-ethyl-4-oxo-pyridazine-5-carboxylic acid 4-Methylphenyl hydrazone of glyoxylic acid (9.2 g at 97%=0.05 mole), dimethyl formamide (0.06 g) and n-hexane (100 ml) were charged to a reaction vessel and thionyl chloride (6.5 g=0.055 mole) was added over 5 minutes with stirring at ambient temperature. The contents were stirred for 2 hours at ambient temperature before decanting off the hexane and replacing it with toluene (100 ml). A calcium hydroxide/methyl-3-oxopentanoate complex made by stirring together methyl-3-oxopentanoate (6.6 g at 98%=0.05 mole), calcium hydroxide (4.7 g at 98%=0.062 mole) and toluene (50 ml) for 2 hours at ambient temperature was added to the reaction vessel and the contents were stirred for 2 hours at ambient temperature. A 2M hydrochloric acid solution (100 ml) was added and stirred for 5 minutes then the two phases were separated. The toluene phase was recharged to the vessel and heated at 80° C. for 2 hours. The contents were cooled at 50° C. and 10% sodium hydroxide solution (50 g) was added. The mixture was then heated at 60°-70° C. for 3 hours then cooled and the two phases separated. The sodium hydroxide phase was added to a rapidly stirred mixture of concentrated sulphuric acid (5.9 g) and water (54.1 g) at ambient temperature over 1 hour. The crude product was recovered by filtration, washed with water until sulphate free and pulled fairly dry. The crude product was charged to isopropanol (25 ml) and heated at reflux for 1 hour before cooling to 20° C. The purified product was recovered by filtration and washed with cold isopropanol then dried at 40°-50° C. and 20 mm Hg pressure.

EXAMPLE 9

Preparation of 1-(4-bromophenyl)-1,4-dihydro-6-ethyl-4-oxo-pyridazine-5-carboxylic acid 4-Bromophenylhydrazone of glyoxylic acid (12.6 g at 97%=0.05 mole), dimethyl formamide (0.6 g) and n-hexane (100 ml) were charged to a reaction vessel and thionyl chloride (6.59=0.055 mole) was added over 5 minutes with stirring at ambient temperature. The contents were stirred for 2 hours at ambient temperature before decanting off the hexane and replacing it with toluene (100 ml). A calcium hydroxide/methyl-3-oxopentanoate complex made by stirring together methyl-3-oxopentanoate (6.6 g at 98%=0.05 mole), calcium hydroxide (4.7 g at 98%=0.062 mole) and toluene (50 ml) for 2 hours at ambient temperature was added to the reaction vessel and the contents were stirred for 2 hours at ambient temperature. A 2M hydrochloric acid solution (100 ml) was added and stirred for 5 minutes then the two phases were separated. The toluene phase was recharged to the vessel and heated at 80° C. for 2 hours. The contents were cooled to 50° C. and 10% sodium hydroxide solution (50 g) was added. The mixture was then heated at 60°-70° C. for 3 hours then cooled and the two phases separated. The sodium hydroxide phase was added to a rapidly stirred mixture of concentrated sulphuric acid (5.9 g) and water (54.1 g) at ambient temperature over 1 hour.

The crude product was recovered by filtration and washed with water until sulphate free then pulled fairly dry. It was then charged to isopropanol (25 ml) and heated at reflux for 1 hour before cooling to 20° C. The purified product was recovered by filtration and washed with cold isopropanol then dried at 40°-50° C. and 20 mm Hg pressure.

EXAMPLE 10

This Example illustrates the use o: different alkaline earth bases in the invention to make the compound 1-(4-chlorophenyl)-1,4-dihydro-6-ethyl-4-oxo-pyridazine-5-carboxylic acid, methyl ester.

The acid chloride of 4-chlorophenylhydrazone (10 g, 0.046M) and methyl-3-oxopentanoate (10.14 g, 0.078M) were mixed together in toluene (100 mls). Alkaline earth metal hydroxide (0.046M) was added and the mixture stirred as the reaction was followed by HPLC. When the reaction was seen to be complete the reaction mixture was treated with 1M hydrochloric acid (95 mls) and after stirring for a short period the aqueous layer was separated ant the organic layer heated to 80° C. for one hour. The toluene solution was then analysed by HPLC for the concentration of the desired product and the yield calculated. The yields for the different alkaline earth metal hydroxides are shown below.

| Base | Yield, % |
| --- | --- |
| Calcium hydroxide | 72.3 |
| Barium hydroxide | 43.6 |
| Lithium hydroxide | 47.1 |

We claim:

1. The method for preparing a pyridazinone derivative having the formula I

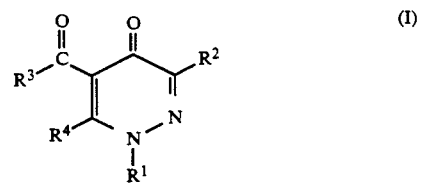

where: $R^1$ is an unsubstituted phenyl group or a phenyl group substituted with alkyl or halo groups, $R^2$ is H, alkyl, or carboxyl groups, $R^3$ is hydroxy or an alkyl or alkoxy group and $R^4$ is an alkyl group; said method comprising reacting a hydrazone of glyoxylic acid halide having formula VII:

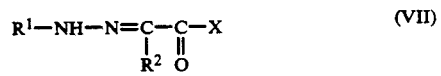

in which X represents a halogen atom and $R^1$ and $R^2$ are as defined above, with either (a) an oxo-carboxylic acid ester having the formula VIII;

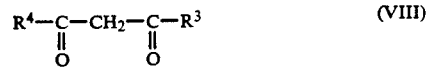

in which $R^3$ is an alkyl or alkoxy group and $R^4$ is as defined above, in the presence of an oxide or hydroxide of a metal selected from the group consisting of calcium, strontium, barium and lithium, or (b) with a preformed complex of an ester (VIII) and an oxide or hydroxide of a metal selected from the group consisting of calcium, strontium, barium and lithium.

2. Method as claimed in claim 1 in which the oxo-carboxylic acid of formula (VIII) is reacted with the oxide or hydroxide of a metal to give a preformed complex, and thereafter contacted with the hydrazone of formula (VII).

3. Method as claimed in claim 1 in which $R^3$ in Formula VIII is alkoxy, and in which the product is subsequently hydrolysed to a compound in which $R^3$ is a hydroxy group.

4. Method as claimed in claim 1 in which the oxide or hydroxide of a metal is calcium hydroxide.

5. Method as claimed in claim 1 in which the oxide or hydroxide of a metal is lithium oxide or hydroxide.

6. Method as claimed in claim 1 which is carried out in an organic liquid medium.

7. Method as claimed in claim 1 in which:
$R^1$ is 4-chlorophenyl; $R^2$ is hydrogen; $R^3$ is hydroxy or alkoxy; and $R^4$ is ethyl.

8. Method as claimed in claim 7 in which $R^3$ is methoxy or ethoxy.

* * * * *

UNITED STATES PATENT AND TRADEMARK OFFICE
CERTIFICATE OF CORRECTION

PATENT NO. : 5,189,163

DATED : February 23, 1993

INVENTOR(S) : Brian G. COX et al

It is certified that error appears in the above-identified patent and that said Letters Patent is hereby corrected as shown below:

On the title page, item [21]:

"Appln. No.: 858,161" should read --Appln. No.: 850,161--.

Signed and Sealed this

Eleventh Day of January, 1994

*Attest:*

BRUCE LEHMAN

*Attesting Officer*   *Commissioner of Patents and Trademarks*